(12) United States Patent
Kantsevitcha et al.

(10) Patent No.: US 6,709,467 B1
(45) Date of Patent: Mar. 23, 2004

(54) ARTERIAL PROSTHESIS

(76) Inventors: Viktoria Kantsevitcha, Lokomotives Iela 72 - 30, LV-1057 Riga (LV); Eriks Masteiko, Lacu Iela 10b, LV-2010 Jurmala (LV); Leonids Ribickis, Dzirnavu Iela 74/76 - 51, LV-1011 Riga (LV)

( * ) Notice: Subject to any disclaimer, the term of this patent is extended or adjusted under 35 U.S.C. 154(b) by 0 days.

(21) Appl. No.: 10/204,009
(22) PCT Filed: May 16, 2000
(86) PCT No.: PCT/LV00/00002

§ 371 (c)(1),
(2), (4) Date: Oct. 10, 2002

(87) PCT Pub. No.: WO01/60426
PCT Pub. Date: Aug. 23, 2001

(30) Foreign Application Priority Data

Feb. 16, 2000 (LV) .................................. P-00-21

(51) Int. Cl.[7] .................................................. A61F 2/06
(52) U.S. Cl. .................. 623/901; 623/1.46; 139/387 R
(58) Field of Search .................... 139/387 R, 383 R, 139/384 R; 623/1.1, 1.41, 1.44, 1.45, 1.46, 901, 1.47, 1.48

(56) References Cited

U.S. PATENT DOCUMENTS

| 4,784,659 A |   | 11/1988 | Fleckenstein |
|---|---|---|---|
| 4,816,028 A | * | 3/1989 | Kapadia et al. ............ 623/1.52 |
| 4,892,539 A | * | 1/1990 | Koch ........................ 623/1.52 |
| 5,127,919 A | * | 7/1992 | Ibrahim et al. ............ 623/1.51 |
| 5,800,514 A | * | 9/1998 | Nunez et al. ............... 623/1.51 |
| 5,904,714 A | * | 5/1999 | Nunez et al. ........... 139/383 R |

FOREIGN PATENT DOCUMENTS

| EP | 0 122 744 A1 | 10/1984 |
|---|---|---|
| EP | 0 183 365 A2 | 6/1986 |
| EP | 0 464 755 A1 | 1/1992 |
| GB | 2 153 685 A | 8/1985 |
| LV | 12175 B | 12/1998 |
| WO | WO 92/03107 | 3/1992 |

* cited by examiner

*Primary Examiner*—Danny Worrell
(74) *Attorney, Agent, or Firm*—Colin P. Abrahams

(57) ABSTRACT

The arterial prosthesis is produced based on weaving technology using biologically inert polyester and polyuretan yarns, braided in a complicated structure. Then the prosthesis is impregnated with a solution of gelatin and glycerin that, when drying up, binds the pores of the prosthesis and the filaments of the polyester yarn.

1 Claim, 1 Drawing Sheet

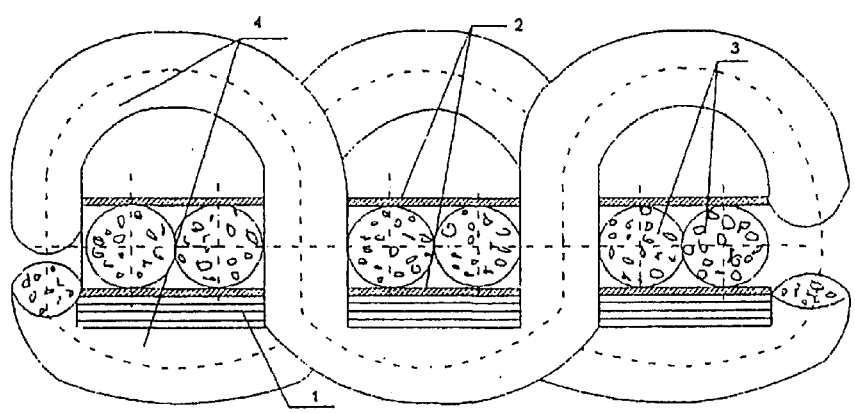

ARTERIAL PROSTHESIS

FIELD AND BACKGROUND OF THE INVENTION

The present invention relates to a medical technique; it can be used in the reconstructive surgery in cases where the circulatory system has congenital anomalies or it suffers from atherosclerosis, injuries or any other detriment.

There exists a flexible blood vessel prosthesis (LV patent No. 12175), consisting of polyester and polyurethan yarns with a lining of velour type crimps on its walls. The said prosthesis represents the following disadvantages:

after implantation the structure of the prosthesis cannot prevent blood leakage through it;

the ends of the prosthesis ravel easily; it makes it difficult to suture the prosthesis to the natural blood vessel.

SUMMARY OF THE INVENTION

The goal of the present invention is to produce an arterial prosthesis that easily modulates when a continues blood flow is pumped through it at a definite pressure and speed. The new prosthesis should exclude blood leakage through its walls, and its ends should be easily attachable to natural blood vessels.

DETAILED DESCRIPTION OF THE INVENTION

The goal is achieved as follows.

The arterial prosthesis is produced using weaving technology. In the weaving machine two warps of polyester yarns are arranged (the number of yarns corresponds to the one that ensures the required diameter of the tube), and two warps of polyurethan yarns. The weft consists of three-yarn systems (one polyester yarn and two polyurethan yarns). All polyurethan yarns are passed to the operational area at a 200% longitudinal stretch. A continuous tube is woven in a complicated braided pattern (two-layered). In each section the cop lays four polyurethan (1) and two polyester (3) yarns (three yarns—from the left towards the right, and three yarns—when returning to the same section from the right to the left, fixing the first three weft yarns on the reed beforehand). The laid weft yarns get compressed between tensioned polyurethan warps (2) and form the intraluminal coat of the prosthesis. The outer surface is formed by polyester warp yarns (4), that lay in a crimpy velour type structure beyond the operational area of the weaving machine when the polyurethan yarns relax.

The arterial prosthesis produced by the said technique, ensures a continuous blood flow; it easily modulates both radially and longitudinally. The internal coat prevents blood from leaking through walls of the prosthesis after implantation, and the interbraiding of both layers forms ends of prosthesis that ravel little. In order to enhance the above features and to ensure safety, the prosthesis gets thermostabilized and vacuum-impregnated with the solution of gelatin and glycerin. When drying up, the solution binds filaments of the polyester yarn and pores of the prosthesis, thus eliminating the permeability of the prosthesis, and its ends become easily attachable to the natural blood vessel (they do not ravel). When implanted, the gelatin and glycerin bonds fill out and through them the natural tissue ingrow, thus forming a dense mesh of capillaries and a stable "neo-intime".

What is claimed is:

1. A method of manufacturing an arterial prosthesis, comprising interbraiding a first woven layer with a second woven layer, the layers being comprised of biologically inert polyester and polyurethane yarns, and applying internal and external coats of gelatin-glycerin solution bonds, such that the arterial prosthesis facilitates pre-stretching of the polyurethane yarns, relaxation of the yarns, to thereby provide a non-permeable prosthesis having a crimp structure, and permitting natural tissue ingrowth into a loose outer layer of the prosthesis.

* * * * *